United States Patent
Hyodo

(10) Patent No.: US 12,178,558 B2
(45) Date of Patent: Dec. 31, 2024

(54) BIOMETRIC INFORMATION PROCESSING APPARATUS AND BIOMETRIC INFORMATION PROCESSING METHOD

(71) Applicant: SONY CORPORATION, Tokyo (JP)

(72) Inventor: Yasuhide Hyodo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1027 days.

(21) Appl. No.: 17/250,313

(22) PCT Filed: May 29, 2019

(86) PCT No.: PCT/JP2019/021190
§ 371 (c)(1),
(2) Date: Dec. 31, 2020

(87) PCT Pub. No.: WO2020/012807
PCT Pub. Date: Jan. 16, 2020

(65) Prior Publication Data
US 2021/0275048 A1    Sep. 9, 2021

(30) Foreign Application Priority Data
Jul. 11, 2018  (JP) .................. 2018-131392

(51) Int. Cl.
*A61B 5/02* (2006.01)
*A61B 5/00* (2006.01)
*A61B 5/024* (2006.01)
*A61B 5/0285* (2006.01)

(52) U.S. Cl.
CPC ...... *A61B 5/02416* (2013.01); *A61B 5/02438* (2013.01); *A61B 5/0285* (2013.01); *A61B 5/7257* (2013.01)

(58) Field of Classification Search
CPC ............ A61B 5/02416; A61B 5/02438; A61B 5/0285; A61B 5/7257
See application file for complete search history.

(56) References Cited

U.S. PATENT DOCUMENTS

| | | |
|---|---|---|
| 2002/0099280 A1 | 7/2002 | Huang |
| 2007/0060827 A1 | 3/2007 | Kobayashi et al. |
| 2021/0290092 A1* | 9/2021 | Hyodo ................. A61B 5/7203 |

FOREIGN PATENT DOCUMENTS

| | | |
|---|---|---|
| CN | 1531407 A | 9/2004 |
| EP | 1757225 A1 | 2/2007 |
| JP | 11-276448 A | 10/1999 |
| JP | 2004-514493 A | 5/2004 |
| JP | 2007-054471 A | 3/2007 |
| WO | 2017/199597 A1 | 11/2017 |
| WO | 2018/055969 A1 | 3/2018 |

OTHER PUBLICATIONS

International Search Report and Written Opinion of PCT Application No. PCT/JP2019/021190, issued on Aug. 13, 2019, 09 pages of ISRWO.

* cited by examiner

*Primary Examiner* — Amanda K Hulbert
(74) *Attorney, Agent, or Firm* — CHIP LAW GROUP

(57) ABSTRACT

To provide a biometric information processing apparatus capable of reducing noise caused by body motion in measuring blood flow velocity. To provide a biometric information processing apparatus including: a first filter unit that selects a first frequency band on the basis of a beat interval, causes a signal of the first frequency band from a blood flow velocity signal to pass through, and extracts a beat component signal.

8 Claims, 11 Drawing Sheets

FIG. 4
| FILTER ID | RANGE OF BEAT INTERVAL | FILTER COEFFICIENT |
|---|---|---|
| 1 | 40 [bpm] ≤ hr_trend < 55 [bpm] | BP1coef_vector1 |
| 2 | 55 [bpm] ≤ hr_trend < 65 [bpm] | BP1coef_vector2 |
| ... | ... | ... |
| N | 180 [bpm] ≤ hr_trend < 200 [bpm] | BP1coef_vectorN |
FIG. 5A
FILTER ID = 2    BP1coef_vector2
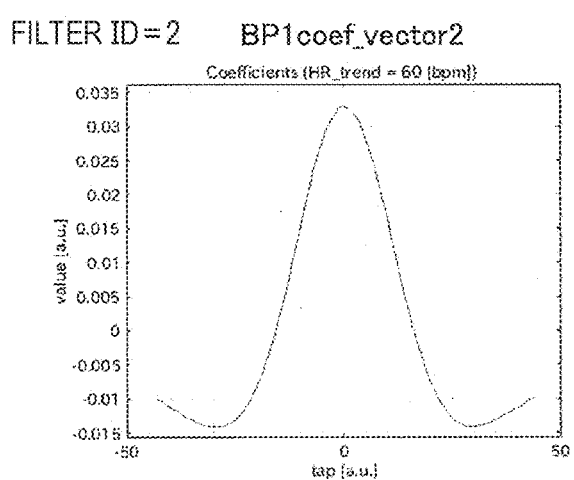
FIG. 5B
FREQUENCY CHARACTERISTICS OF BP1coef_vector2
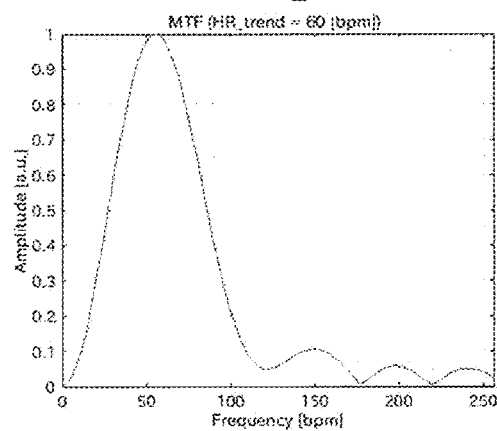

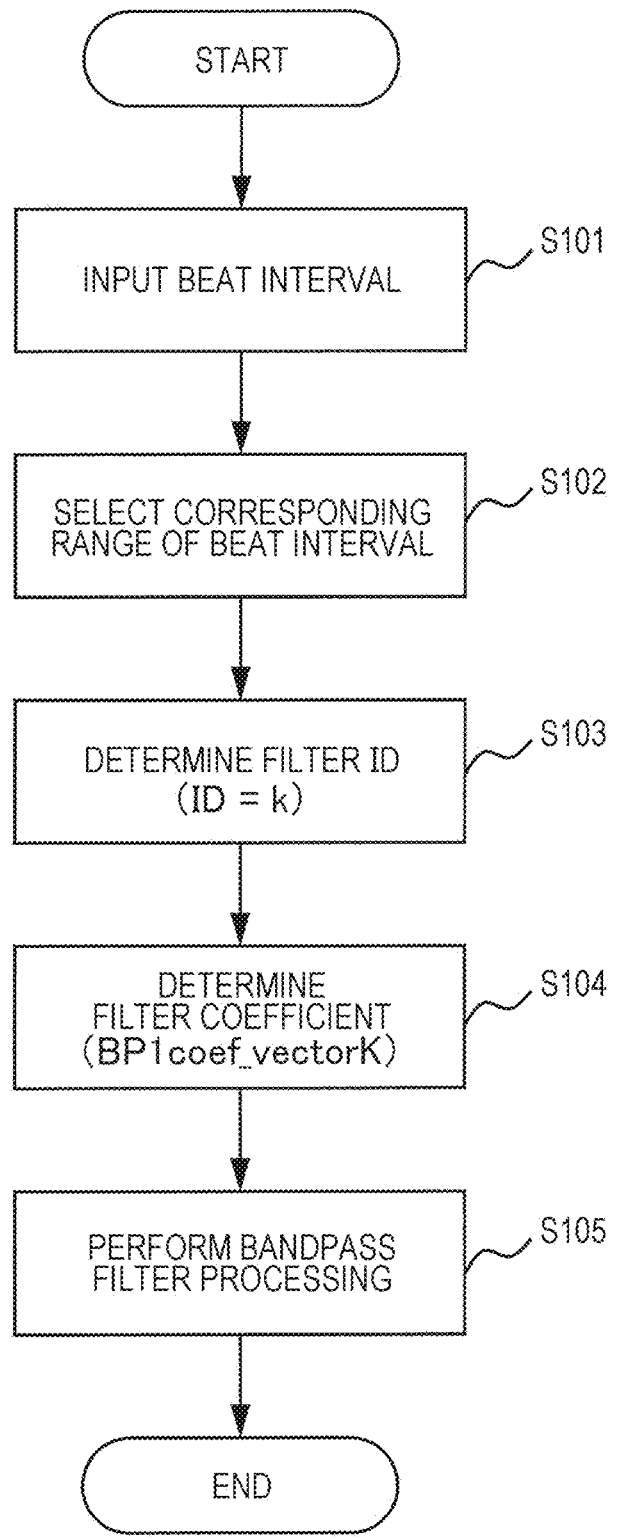

| FILTER ID | RANGE OF BEAT INTERVAL | FILTER COEFFICIENT |
|---|---|---|
| 1 | 40 [bpm] ≤ hr_trend < 55 [bpm] | BP2coef_vector1 |
| 2 | 55 [bpm] ≤ hr_trend < 65 [bpm] | BP2coef_vector2 |
| ... | ... | ... |
| N | 180 [bpm] ≤ hr_trend < 200 [bpm] | BP2coef_vectorN |

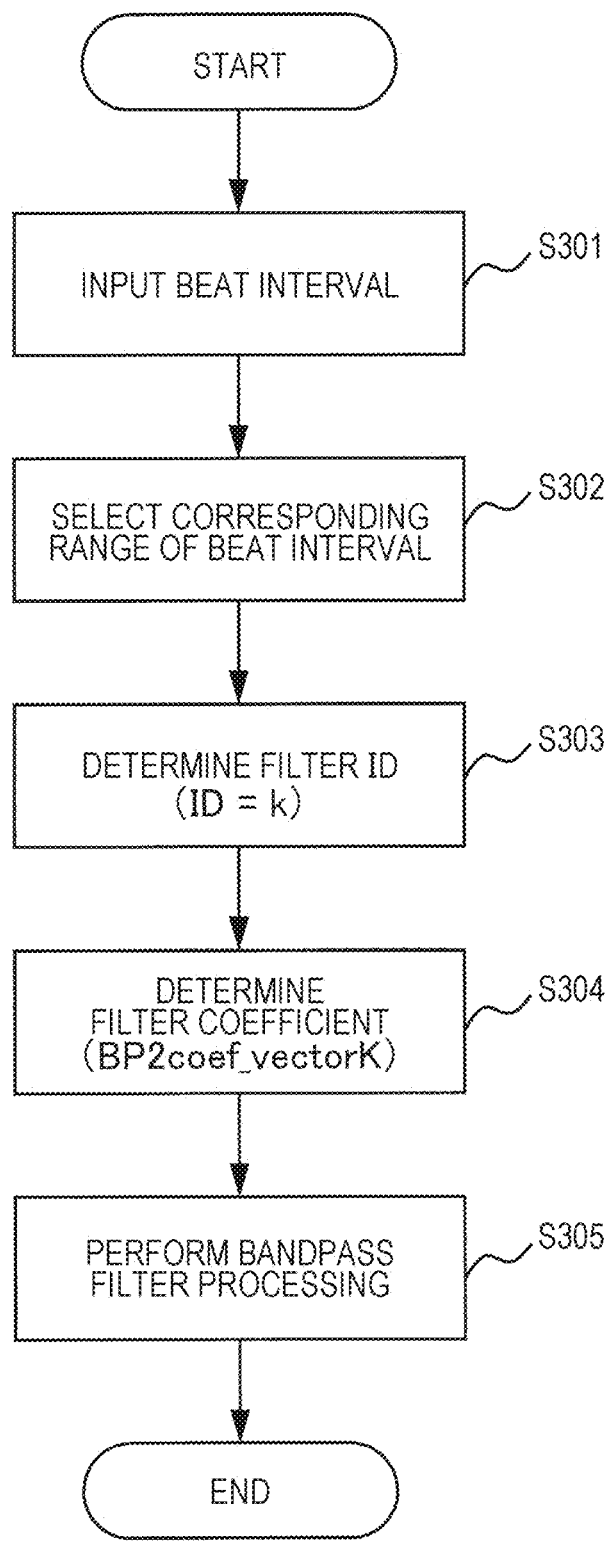

BEAT COMPONENT SIGNAL

BP2coef_vector2

PEAK POSITION LIKELIHOOD

BIOMETRIC INFORMATION PROCESSING APPARATUS AND BIOMETRIC INFORMATION PROCESSING METHOD

CROSS REFERENCE TO RELATED APPLICATIONS

This application is a U.S. National Phase of International Patent Application No. PCT/JP2019/021190 filed on May 29, 2019, which claims priority benefit of Japanese Patent Application No. JP 2018-131392 filed in the Japan Patent Office on Jul. 11, 2018. Each of the above-referenced applications is hereby incorporated herein by reference in its entirety.

TECHNICAL FIELD

The present technology relates to a biometric information processing apparatus and a biometric information processing method. More specifically, the present invention relates to a biometric information processing apparatus and a biometric information processing method for measuring blood flow velocity.

BACKGROUND ART

In recent years, with the boom in healthcare and wellness, a technology for measuring a person's physiological response in daily life and sensing the health state and the psychological state has attracted attention. When a person's psychological state changes, signals are transmitted from the brain via the autonomic nervous system, causing changes in functions such as respiration, skin temperature, sweating, heart, and vascular activity. Since the timing of diastole and systole of the ventricle and cardiac output change as the psychological state changes, it is known that the psychological state can be sensed by detecting changes in blood flow velocity according to the systole and diastole of the ventricle at fingertips, wrists, earlobes, forehead, or the like. In this way, blood flow velocity is attracting attention as one index showing a person's psychological state.

When measuring a person's physiological response, when the site being measured moves, noise due to body motion (body motion noise) is generated in an observation signal and the S/N ratio decreases. Therefore, a technology for reducing the body motion noise to improve the accuracy of measurement has been studied.

For example, Patent Document 1 describes a technology having an object of obtaining an accurate pulse rate. Patent Document 2 describes a technology having an object of enabling accurate heartbeat measurement.

CITATION LIST

Patent Document

Patent Document 1: Japanese Patent Application Laid-Open No. 11-276448
Patent Document 2: WO 2018/055969 A

SUMMARY OF THE INVENTION

Problems to be Solved by the Invention

The technologies of Patent Documents 1 and 2 described above are technologies related to measurement of pulse rate and heart rate. However, for blood flow velocity, which has been attracting attention in recent years as an index showing a psychological state, a technology for reducing body motion noise has not been established, and improvement in measurement accuracy has been required.

Therefore, a main object of the present technology is to provide a biometric information processing apparatus capable of reducing noise caused by body motion in measuring blood flow velocity.

Solutions to Problems

That is, the present technology provides a biometric information processing apparatus including: a first filter unit that selects a first frequency band on the basis of a beat interval, causes a signal of the first frequency band from a blood flow velocity signal to pass through, and extracts a beat component signal.

The biometric information processing apparatus may further include:
a peak detection unit that detects a peak position of the beat component signal and outputs peak time and beat component intensity at the peak time, in which
the peak detection unit
detects the peak position of the beat component signal on the basis of the beat interval and holds the beat component intensity as history information except when body motion occurs,
determines whether or not detection of the peak position is erroneous on the basis of the history information after detecting the peak position of the beat component signal on the basis of the beat interval and the history information when body motion occurs, and, in a case where the detection of the peak position is erroneous, corrects the peak position by using the beat interval and corrects the beat component intensity by using the history information.

The first filter unit may include a first filter bank including a plurality of bandpass filters and may use a bandpass filter selected from the first filter bank on the basis of the beat interval to extract the beat component signal.

The peak detection unit may include a second filter unit that selects a second frequency band on the basis of the beat interval except when body motion occurs, cause a signal of the second frequency band from the beat component signal to pass through, and detect the peak position of the beat component signal.

The second filter unit may include a second filter bank including a plurality of bandpass filters and use a bandpass filter selected from the second filter bank on the basis of the beat interval to detect the peak position of the beat component signal except when body motion occurs.

When body motion occurs, in a case where the detection of the peak position is erroneous, the peak detection unit may calculate likelihood of probability distribution of the peak position according to the beat interval, and set a peak position where the likelihood is maximum as a corrected peak position.

Furthermore, the present technology provides a biometric information processing method including: a first filter process of selecting a first frequency band on the basis of a beat interval, causing a signal of the first frequency band from a blood flow velocity signal to pass through, and extracting a beat component signal.

Effects of the Invention

According to the present technology, it is possible to provide a biometric information processing apparatus capable of reducing noise caused by body motion in measuring blood flow velocity. Note that effects of the present technology are not necessarily limited, but may also be any of those described in the present description.

BRIEF DESCRIPTION OF DRAWINGS

FIG. 4 is a table showing an example of data stored in a first filter bank.

FIGS. 5A and 5B are graphs showing an example of a bandpass filter.

FIG. 6 is a flowchart showing an example of a first filter process.

FIG. 10 is a flowchart showing an example of a second filter process.

MODE FOR CARRYING OUT THE INVENTION

Hereinafter, a preferred mode for carrying out the present technology will be described with reference to the drawings. Note that embodiments described below indicate representative embodiments of the present technology, and they do not make the scope of the present technology to be understood narrowly. Note that description will be presented in the following order.

Figure 1A:
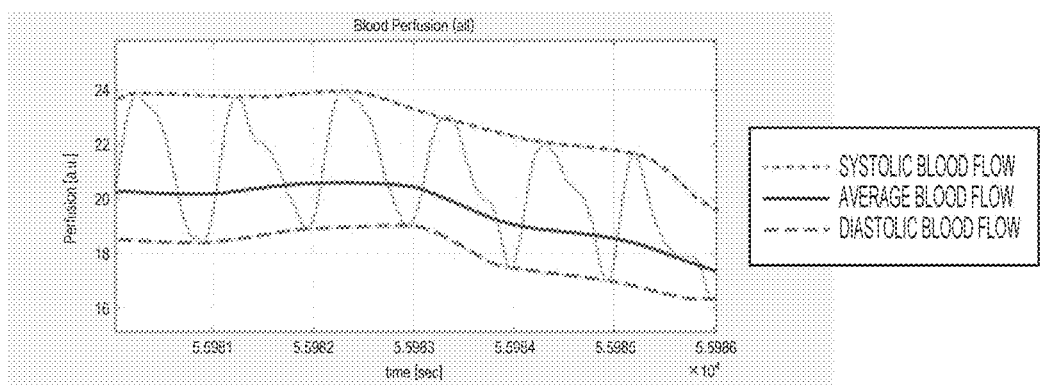
FIGS. 1A and 1B are schematic diagrams showing an example of a blood flow velocity signal.
Figure 1B:
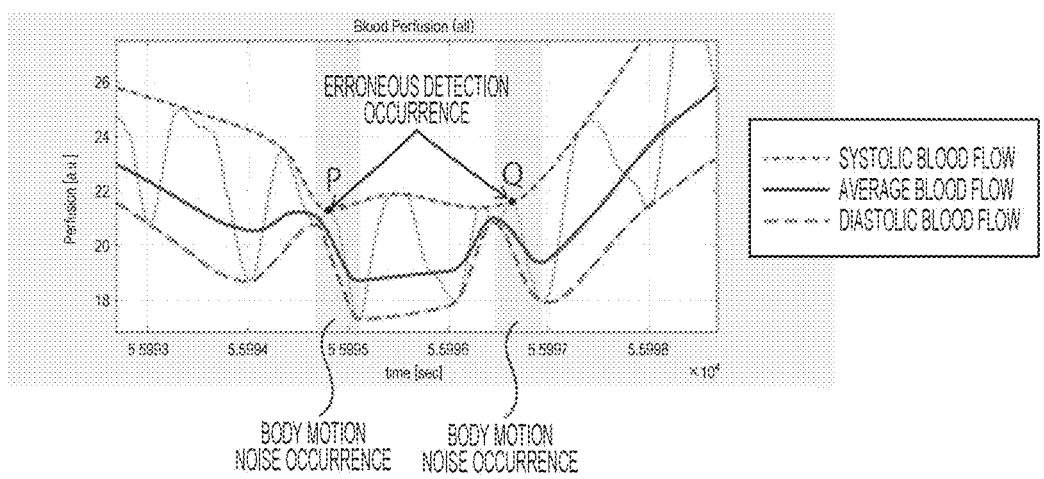

1. Description of blood flow velocity signal at rest and when body motion occurs
2. First Embodiment
   (1) Configuration of biometric information processing apparatus 1
   (2) Operation of biometric information processing apparatus 1
3. First variation example of the first embodiment
4. Second variation example of the first embodiment 1. Description of Blood Flow Velocity Signal at Rest and when Body Motion Occurs FIGS. 1A and 1B are schematic diagrams showing an example of a blood flow velocity signal. FIG. 1A is a blood flow velocity signal at rest, and FIG. 1B is a blood flow velocity signal when body motion occurs. A peak P and a peak Q in FIG. 1B indicate false peaks due to body motion.

For example, in a case where changes in a person's psychological state are sensed by changes in blood flow velocity according to systole and diastole of a ventricle, the peak position of the blood flow velocity signal needs to be detected more accurately to measure blood flow in systole and diastole. As shown in FIG. 1A, when the body motion of a measurement subject is not occurring, that is, when the measurement subject is at rest, the peak in the blood flow velocity signal is observed along with the beating of the heart, and therefore it is unlikely that an error will occur in the detection of the peak position. On the other hand, as shown in FIG. 1B, when body motion noise occurs due to the body motion of the measurement subject and false peaks (peak P and peak Q) not accompanied by beating are observed, the peak positions are likely to be erroneously detected. Therefore, in order to avoid erroneous detection of the peak position and more accurately detect changes in blood flow velocity, it is necessary to reduce the body motion noise.

As described above, there is a demand for a technology for reducing the body motion noise in order to more accurately detect the peak position of the blood flow velocity signal in the measurement of the blood flow velocity. The present technology provides a technology for reducing the body motion noise in measurement of the blood flow velocity.

2. First Embodiment (1) Configuration of Biometric Information Processing Apparatus 1

The configuration of the biometric information processing apparatus 1 according to the first embodiment will be described with reference to FIG. 2.

Figure 2:
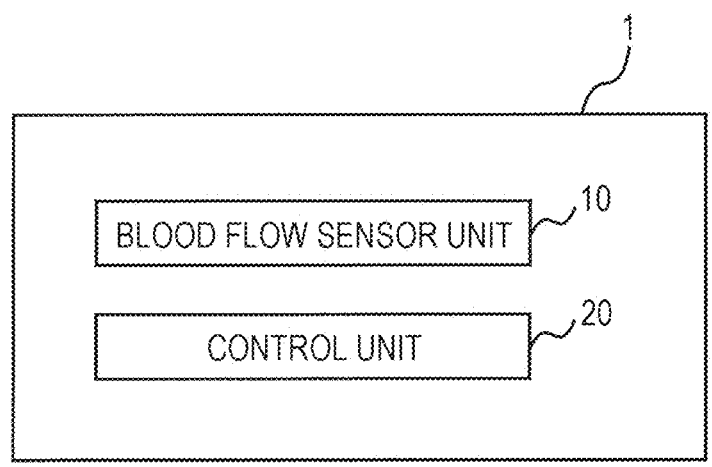
FIG. 2 is a diagram showing a configuration example of a biometric information processing apparatus according to a first embodiment.

FIG. 2 is a diagram showing a configuration example of the biometric information processing apparatus 1 according to the first embodiment. The biometric information processing apparatus 1 includes a blood flow sensor unit 10 and a control unit 20.

Embodiments of the biometric information processing apparatus 1 include, for example, various wearable apparatuses such as of a headband type, a neckband type, a belt type, and the like; any personal digital assistant (PDA) such as a smartphone, a tablet terminal, or the like; any electronic equipment such as medical equipment, game equipment, home appliance equipment, or the like; and the like. The biometric information processing apparatus 1 may include physically one apparatus or may include physically a plurality of apparatuses. For example, the biometric information processing apparatus 1 may include a wearable apparatus having the function of a blood flow sensor 10 and a personal digital assistant which is communicably connected to the wearable apparatus and has the function of the control unit 20.

The configuration of the blood flow sensor unit 10 is not particularly limited as long as it can measure the blood flow. As the blood flow sensor unit 10, for example, a laser Doppler flowmetry (LDF) can be adopted. The laser Doppler flowmetry can irradiate a human skin surface with a laser beam to measure blood flow in capillaries non-invasively and continuously, and is small in size. Therefore, the laser Doppler flowmetry is suitable for wearable apparatuses that can be easily worn by the measurement subject in daily life.

The control unit 20 includes hardware necessary for a computer, such as a CPU and memory (RAM, ROM). When the CPU calls programs and data recorded on a ROM or the like onto a RAM and executes processing, the overall control and functions of the biometric information processing apparatus 1 are realized. As the control unit 20, for example, a programmable logic device (PLD) such as a field programmable gate array (FPGA) or another device such as an application specific integrated circuit (ASIC) may be used.

Figure 3:
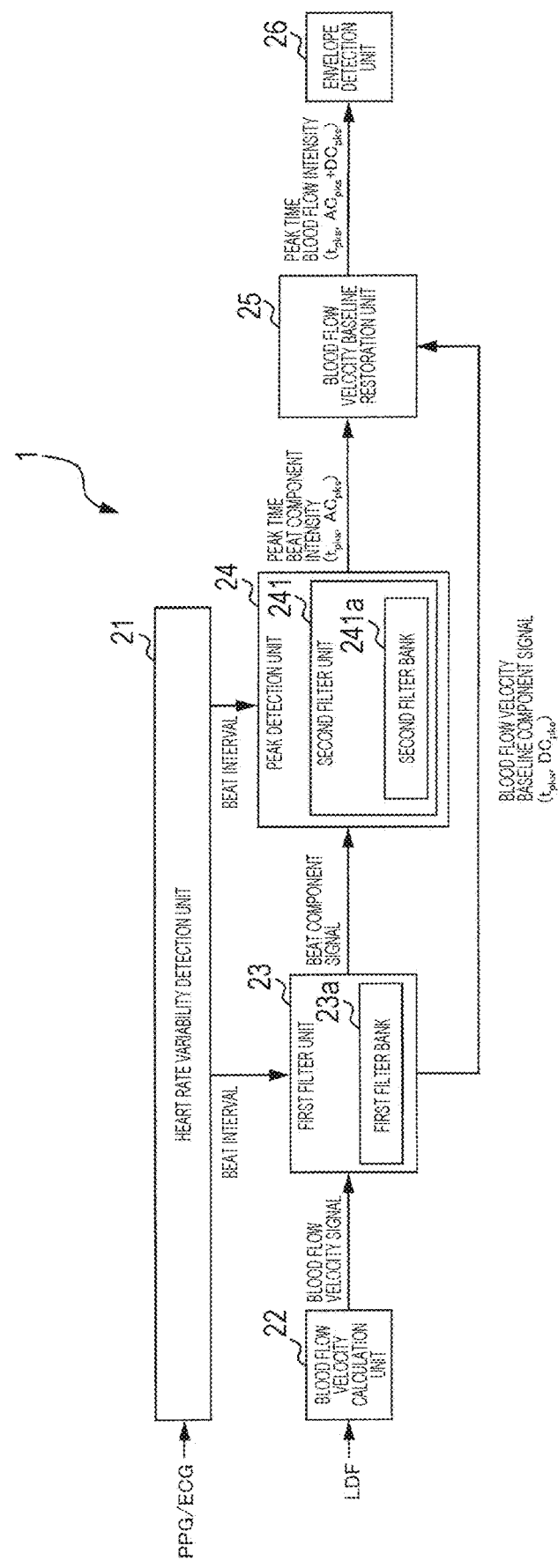
FIG. 3 is a block diagram showing an example of a functional configuration of a biometric information processing apparatus according to the first embodiment.

FIG. 3 is a block diagram showing an example of a functional configuration of the biometric information processing apparatus 1 according to the first embodiment. A heart rate variability detection unit 21, a blood flow velocity calculation unit 22, a first filter unit 23, a peak detection unit 24, a blood flow velocity baseline restoration unit 25, and an envelope detection unit 26 are realized by the control unit 20.

(2) Operation of Biometric Information Processing Apparatus 1

Next, an operation of the biometric information processing apparatus 1 according to the first embodiment is described with reference to FIG. 3.

The heart rate variability detection unit 21 executes a heart rate variability detection process of detecting the heart rate variability of the measurement subject, and outputs a beat interval. In FIG. 3, "PPG" indicates a photoplethysmography-type (PPG type) pulse wave sensor, and "ECG" means an electrocardiogram. In the present embodiment, the heart rate variability detection unit 21 detects the heart rate variability on the basis of information obtained from the PPG type pulse wave sensor or the electrocardiogram, and calculates the beat interval.

The blood flow velocity calculation unit 22 executes a blood flow velocity calculation process of calculating the blood flow velocity of the measurement subject, and outputs a blood flow velocity signal. In FIG. 2, "LDF" means a laser Doppler flowmetry, indicating a case where the blood flow sensor unit 10 (FIG. 2) is a laser Doppler flowmetry. The blood flow velocity (perfusion) can be calculated by the following Formula (I) from a beat signal observed as reflection light obtained by irradiating the human skin surface with a laser beam laser light.

[Math. 1]

$$(\text{Perfusion}) = \frac{\int \omega P(\omega) d\omega}{\int P(\omega) d\omega} \quad (\text{I})$$

In the Formula (I) described above, $\omega$ represents frequency and $P(\omega)$ represents frequency spectrum density function. Note that the method for calculating the blood flow velocity is not limited to the above-mentioned method.

The first filter unit 23 executes the first filter process of extracting a beat component signal from the blood flow velocity signal output from the blood flow velocity calculation unit 22. The beat component signal is a variable component (alternating current component: AC component) associated with beating included in the blood flow velocity signal.

Except when the body motion occurs (at rest), the peak in the blood flow velocity signal is detected with the beating, and the time between the peaks is separated by the beat interval. On the other hand, when the body motion occurs, a false peak having a low correlation with the beat interval occurs in the blood flow velocity signal. The first filter unit 23 executes the first filter process of extracting a beat component signal from the blood flow velocity signal by using the information of beat interval to remove the false peaks not associated with the beating, which are the body motion noise. That is, the biometric information processing apparatus 1 of the present embodiment can reduce the body motion noise in the blood flow velocity signal by executing the first filter process.

In the first filter process, the first filter unit 23 selects a first frequency band on the basis of the beat interval output from the heart rate variability detection unit 21, and performs filter processing causing a signal of the first frequency band from among the blood flow velocity signal described above to pass through. By this filter processing, the first filter unit 23 extracts the beat component signal.

Bandpass filter processing can be adopted as the filter processing described above in the first filter unit 23. In order to execute the bandpass filter processing, the first filter unit 23 can include a first filter bank 23a including a plurality of bandpass filters. The first filter unit 23 can select a bandpass filter from the first filter bank 23a on the basis of the beat interval output from the heart rate variability detection unit 21 and use the bandpass filter to extract beat component signal described above. The first filter bank 23a holds the plurality of bandpass filters as filter coefficients corresponding to each filter.

FIG. 4 is a table showing an example of data stored in the first filter bank 23a. In the first filter bank 23a, filter IDs (1, 2, . . . N) of each bandpass filter, the range of the beat interval, and the filter coefficients are stored in association with one another. In the example shown in FIG. 4, N types of filter coefficients corresponding to the beat interval from 40 bpm to 200 bpm are shown.

For example, in the item of which filter ID is 2, a conditional expression (55 bpm≤hr_trend<65 bpm) for the case where the beat interval (hr_trend) is 55 bpm or more and less than 65 bpm is stored as the range of beat interval. Furthermore, the data of BP1coef_vector2 is stored as the filter coefficient.

FIGS. 5A and 5B are graphs showing an example of the bandpass filter. FIG. 5A is a graph of filter coefficient (BP1coef_vector2) in a case where the filter ID is 2. The horizontal axis of FIG. 5A is the number of taps, and the vertical axis is the filter coefficient. The bandpass filter is constructed using the filter coefficients shown in FIG. 5A.

FIG. 5B is frequency characteristics of a bandpass filter using the filter coefficient of the filter ID 2. The horizontal axis of FIG. 5B is frequency, and the vertical axis is the intensity (transmittance) of the signal passing through the bandpass filter. By confirming the frequency characteristics of BP1coef_vector2 in FIG. 5B, it can be understood that filter characteristics that allow only the band around a beat interval of 60 bpm to pass through can be provided. Note that it is sufficient if the frequency characteristics of the bandpass filter are appropriately set for the purpose of extracting the beat component signal from the blood flow velocity signal.

In this way, it is possible to select the bandpass filter corresponding to each beat interval from the plurality of filter coefficients stored in the first filter bank 23a. Therefore, it is possible to perform appropriate filter processing for each range of the beat interval, and it is possible to extract the beat component signal from the blood flow velocity signal.

FIG. 6 is a flowchart showing an example of the first filter process executed by the first filter unit 23. First, the beat interval is input to the first filter unit 23 (step S101). The first filter unit 23 selects the corresponding range of the beat interval from the first filter bank 23a (step S102) and determines the corresponding filter ID (step S103). Describing with the example shown in FIGS. 5A and 5B, in a case where the beat interval input in step S101 is 60 bpm, it is determined that the beat interval is included in the range of 55 bpm or more and less than 65 bpm, and ID=2 is determined as the filter ID.

The first filter unit 23 determines the filter coefficient from the filter ID (step S104). Describing with the example shown in FIGS. 5A and 5B, the filter coefficient in a case where ID=2 is determined is BP1coef_vector2. In this way, the bandpass filter to pass through the frequency band including the input beat interval is determined. The pass band of the determined filter coefficient corresponds to the first frequency band described above in the present embodiment.

The first filter unit 23 selects a bandpass filter from the determined filter coefficient, and performs the bandpass filter processing using the bandpass filter (step S105). The bandpass filter processing removes bands other than the beat component, and extracts the beat component signal from the blood flow velocity signal. In this way, the first filter unit 23 can remove noise (body motion noise) caused by the body motion from the blood flow velocity signal.

Returning to FIG. 3, the first filter unit 23 will be further described. In the first filter process, the first filter unit 23 holds a signal on the lower frequency side than the beat component signal of the band other than the beat component removed in the processing of extracting the beat component signal as a blood flow velocity baseline component signal, and outputs it. The blood flow velocity baseline component signal is a baseline component (direct current component: DC component) associated with the beating included in the blood flow velocity signal. The blood flow velocity baseline component signal is input to the blood flow velocity baseline restoration unit 25, which will be described later.

The peak detection unit 24 executes the peak detection process of detecting the peak position of the beat component signal output from the first filter unit 23, and outputs the peak time and the beat component intensity at the peak time. The peak detection unit 24 holds the beat component intensity as history information or corrects the beat component intensity depending on whether or not the body motion is occurring. Therefore, the body motion noise can be further reduced and the accuracy of peak position detection can be improved.

Figure 7:
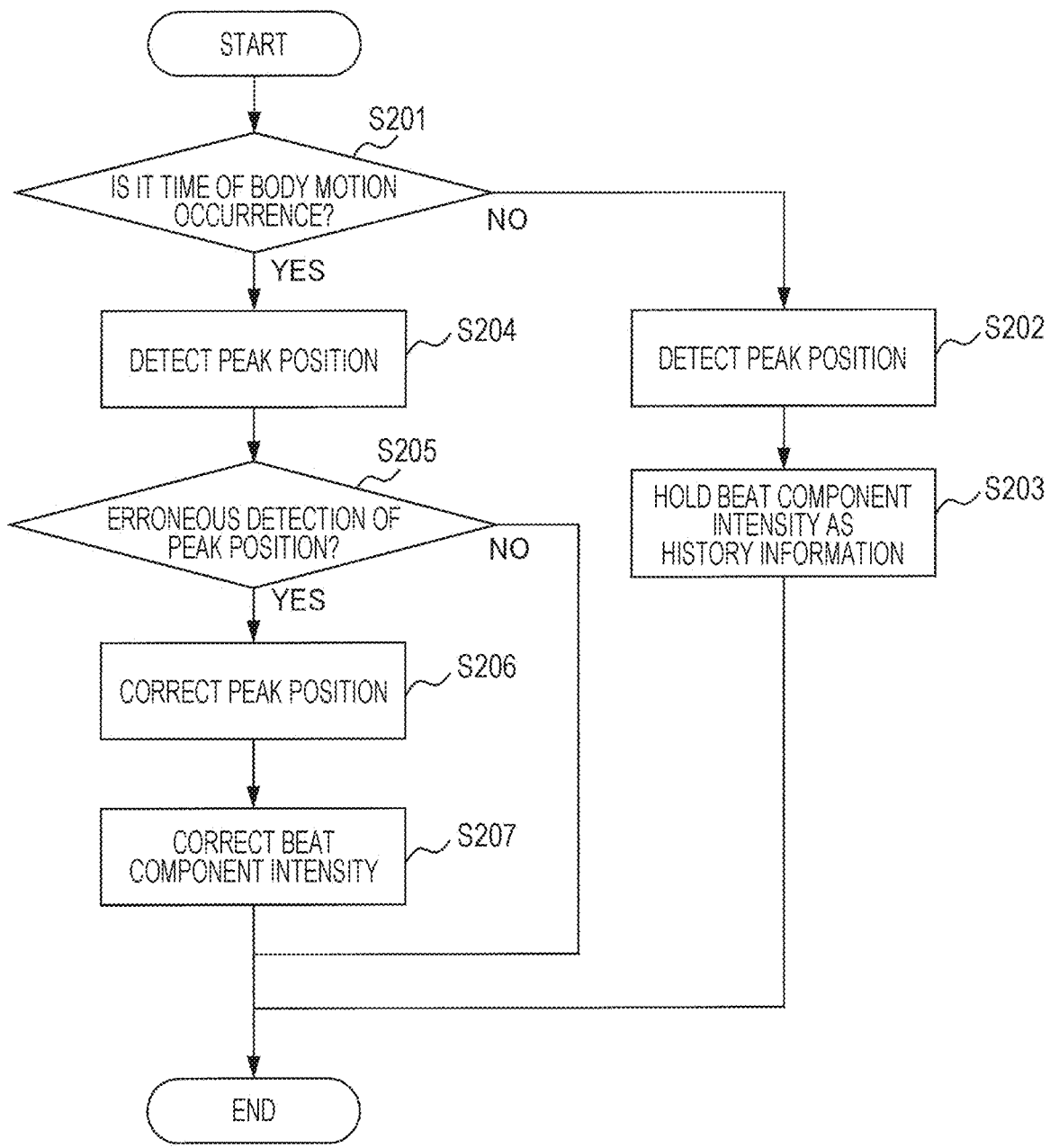
FIG. 7 is a flowchart showing an example of a peak detection process.

FIG. 7 is a flowchart showing an example of the peak detection process executed by the peak detection unit 24. Regarding the processing in the peak detection unit 24, first, the entire flow will be described with reference to FIG. 7.

The peak detection unit 24 determines whether it is when the body motion occurs or except when the body motion occurs (step S201). Whether or not the body motion is occurring is only required to be determined by adopting or applying a known technique for detecting the body motion. For example, the determination may be made on the basis of an output result of an acceleration sensor or a gyro sensor, or may be made depending on whether or not the waveform of the blood flow signal output from the blood flow sensor unit 10 is disturbed. Furthermore, the data of the blood flow signal output from the blood flow sensor unit 10 may be accumulated and learned by artificial intelligence (AI), whether or not the body motion is occurring may be determined by the artificial intelligence.

In a case where it is determined to be except when the body motion occurs (step S201: NO), the peak position of the beat component signal is detected on the basis of the beat interval (step S202), and the beat component intensity is held as history information (step S203). In step S202, the beat interval is a beat interval output from the heart rate variability detection unit 21, and the beat component signal is a beat component signal output from the first filter unit 23.

In a case where it is except when the body motion occurs, the body motion noise is small and the signal quality of the beat component signal is high, and the peak component associated with the beating is sufficiently held. Therefore, in steps S202 and S203, the peak position is detected on the basis of the beat interval, and the beat component intensity with less influence of the body motion and high reliability is held as history information.

On the other hand, in a case where it is determined that the time is when the body motion is occurring (step S201: YES), the peak position of the beat component signal is detected on the basis of the beat interval and the history information (step S204). In step S204, the beat interval is a beat interval output from the heart rate variability detection unit 21, and the history information includes the beat component intensity held in step S203 described above. The history information may include beat component intensity information other than the beat component intensity held in step S203. For example, the peak detection unit 24 may hold in advance the beat component intensity acquired before executing the peak detection peak detection process as history information. For example, the peak detection unit 24 may hold in advance the beat component intensity that is based on the result of blood flow velocity measured with the measurement subject in a resting state to avoid influence by the body motion, as history information.

The peak detection unit 24 determines whether or not the detection of the peak position is erroneous on the basis of the history information (step S205). For example, the difference between the beat component intensity of the detected peak and the beat component intensity included in the history information may be calculated, and when the difference is equal to or greater than a threshold value, it may be determined that the detected peak position is erroneous.

In a case where the peak position detection is not erroneous (step S205: NO), the processing ends. In a case where the peak position is detected erroneously (step S205: YES), the beat interval is used to correct the peak position (step S206), and the history information is used to correct the beat component intensity (step S207). The beat interval of step S206 and the history information of step S207 are similar to the beat interval and the history information described in step S204 described above. Note that regarding the order of steps S206 and S207, whichever may come first or they may come simultaneously.

In a case where the body motion occurs, there can be a case where it is desired to further improve the signal quality of the beat component signal even when the body motion noise is reduced by the first filter unit 23. The peak detection unit 24 improves the accuracy of peak position detection by using the history information in which the highly reliable beat component intensity is held as a history in combination with the beat interval (step S204). Furthermore, the peak detection unit 24 improves the signal quality by correcting the peak position and the beat component intensity when an erroneous detection is found (steps S206 and 207). In this way, the peak detection unit 24 realizes further reduction in body motion noise.

In the processing of correcting the beat component intensity (step S207), for example, the beat component intensity held as the history information is only required to be output as the corrected beat component intensity.

Next, regarding the processing in the peak detection unit 24, an example of the step of correcting the peak position using the beat interval when the body motion occurs (step S206 in FIG. 7) will be described with reference to FIG. 8.

Figures 8, 9:
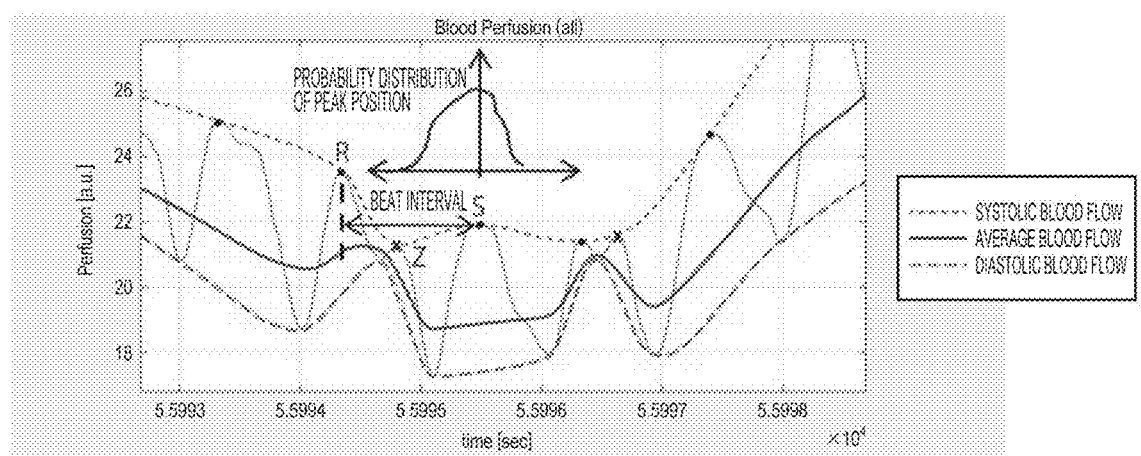
FIG. 8 is a diagram for explaining an example of correction of a peak position when body motion occurs.
FIG. 9 is a table showing an example of data stored in a second filter bank.

FIG. 8 is a diagram for explaining an example of correction of a peak position when body motion occurs. In FIG. 8, the x mark on the blood flow velocity signal is a false peak caused by body motion noise, and the black circle mark is a true peak.

In a case where the peak detection unit 24 determines that the detection of the peak position is erroneous when the body motion occurs, the peak detection unit 24 calculates the likelihood of probability distribution of the peak position according to the beat interval, and can set the peak having the maximum likelihood as the corrected peak position. In this way, the peak detection unit 24 can correct the peak position.

In the example shown in FIG. 8, the probability that starting from the peak position of a detected true peak R, a next peak S separated by the beat interval is a true peak is the highest. In a case where a false peak Z is erroneously detected as a true peak, the likelihood of probability distribution of the peak position is calculated according to the beat interval and the peak position of the peak S having the maximum likelihood is used to correct the peak position of the false peak Z. Specifically, the position of the peak next to the peak R is corrected to the position of the peak S instead of the position of the peak Z.

Next, regarding the processing in the peak detection unit 24, the step of detecting the peak position except when the body motion occurs (step S202 in FIG. 7) will be further described with reference to FIGS. 3 and 9.

Except when the body motion occurs, there is little body motion noise and the signal quality of the beat component signal is high. However, in a case where the possibility of a false peak occurring in the beat component signal cannot be completely ruled out, a false peak can occur, leading to erroneous detection of the peak. Therefore, the peak detection unit 24 detects the peak position according to the beat interval by executing the second filter process described below, and further reduces the body motion noise.

As shown in FIG. 3, the peak detection unit 24 can include a second filter unit 241. The second filter unit 241 executes the second filter process that selects a second frequency band on the basis of the beat interval except when body motion occurs and detects the peak position of the beat component signal by performing the filter processing causing a signal of the second frequency band from the beat component signal to pass through. This beat component signal is a beat component signal output from the first filter unit 23.

Bandpass filter processing can be adopted as the filter processing in the second filter unit 241. In order to execute the bandpass filter processing, the second filter unit 241 can include a second filter bank 241a including a plurality of bandpass filters. The second filter unit 241 can select a bandpass filter from the second filter bank 241a on the basis of the beat interval output from the heart rate variability detection unit 21 except when body motion occurs and use the bandpass filter to detect the peak position of the beat component signal described above. The second filter bank 241a holds the plurality of bandpass filters as filter coefficients corresponding to each filter.

FIG. 9 is a table showing an example of data stored in the second filter bank 241a. In the second filter bank 241a, filter IDs (1, 2, . . . N) of each bandpass filter, the range of the beat interval, and the filter coefficients are stored in association with one another. In the example shown in FIG. 9, N types of filter coefficients corresponding to the beat interval from 40 bpm to 200 bpm are shown.

For example, in the item of which filter ID is 2, a conditional expression (55 bpm≤hr_trend<65 bpm) for the case where the beat interval (hr_trend) is 55 bpm or more and less than 65 bpm is stored as the range of beat interval. Furthermore, the data of BP2coef_vector2 is stored as the filter coefficient.

FIG. 10 is a flowchart showing an example of the second filter process executed by the second filter unit 241. First, the beat interval is input to the second filter unit 241 (step S301). The second filter unit 241 selects the corresponding range of the beat interval from the second filter bank 241a (step S302) and determines the corresponding filter ID (step S303). Describing with the example shown in FIG. 9, in a case where the beat interval input in step S301 is 60 bpm, it is determined that the beat interval is included in the range of 55 bpm or more and less than 65 bpm, and ID=2 is determined as the filter ID.

The second filter unit 241 determines the filter coefficient from the filter ID (step S304). Describing with the example shown in FIG. 9, the filter coefficient in a case where ID=2 is determined is BP2coef_vector2. In this way, the bandpass filter to pass through the frequency band including the input beat interval is determined. The pass band of the determined filter coefficient corresponds to the second frequency band described above in the present embodiment.

The second filter unit 241 selects a bandpass filter from the determined filter coefficient, and performs the bandpass filter processing using the bandpass filter (step S305). The peak position of the beat component signal is detected by the bandpass filter processing.

Figure 11A:
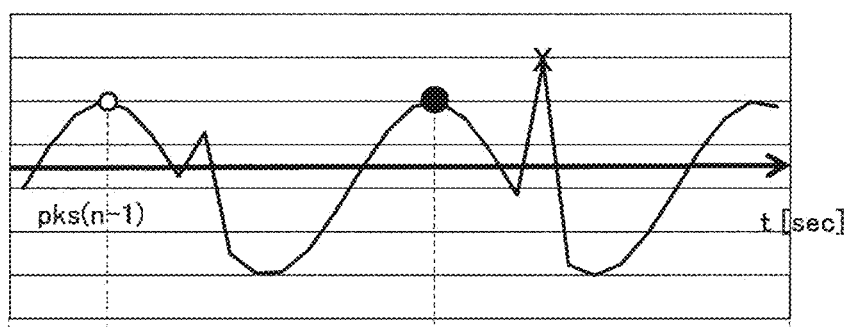
FIGS. 11A, 11B, and 11C are diagrams for explaining an example of the second filter process.
Figure 11B:
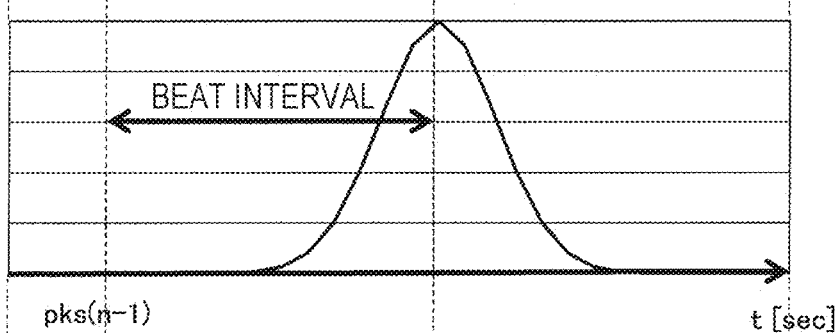
Figure 11C:
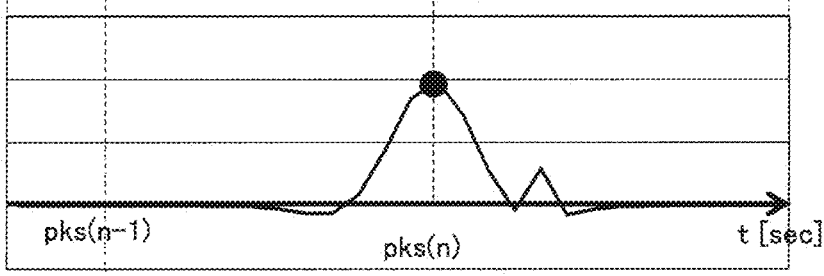

FIGS. 11A, 11B, and 11C are diagrams for explaining an example of the second filter process. In FIG. 11A, the white circle on the beat component signal is the current peak position, the black circle is the true peak, and the x mark is the false peak. For example, as shown in FIG. 11B, the filter coefficient is determined to be BP2coef_vector2 from the second filter bank 241a (FIG. 9), and is superimposed on the beat component signal shown in FIG. 11A. As a result, as shown in FIG. 11C, it is possible to emphasize only the intensity of the true peak according to the beat interval and reduce the intensity of the false peak. In this way, the second filter unit 241 can reduce the body motion noise and accurately detect the peak position of the beat component signal.

Returning to FIG. 3, next, the blood flow velocity baseline restoration unit 25 will be described. The blood flow velocity baseline restoration unit 25 executes a blood flow velocity baseline restoration process that adds the blood flow velocity baseline component signal output from the first filter unit 23 and the peak time and the beat component intensity output from the peak detection unit 24. Therefore, the blood flow velocity baseline restoration unit 25 restores the blood flow intensity and outputs the peak time and the blood flow intensity.

The blood flow velocity baseline component at an arbitrary peak time ($t_{pks}$) output from the first filter unit 23 is described as "$t_{pks}, DC_{pks}$", and the beat component intensity at a peak time ($t_{pks}$) output from the peak detection unit 24 is described as "$t_{pks}, AC_{pks}$". In this case, the blood flow intensity at the peak time ($t_{pks}$) output from the blood flow velocity baseline restoration unit 25 is "$t_{pks}, AC_{pks}+DC_{pks}$".

The envelope detection unit 26 executes an envelope detection process that calculates the envelope of the blood flow velocity signal by interpolating one-dimensional data between peaks with respect to a data string of the peak time and the blood flow intensity ($t_{pks}, AC_{pks}+DC_{pks}$) output from the blood flow velocity baseline restoration unit 25. In the one-dimensional data interpolation, the curve of the envelope is calculated by using a known algorithm such as Cubic interpolation that smoothly interpolates between peaks.

By the operation described in detail above, the biometric information processing apparatus 1 of the present embodiment outputs a blood flow velocity signal with reduced body motion noise.

Since the biometric information processing apparatus of the present technology can reduce the body motion noise in measuring blood flow velocity, it is effective in all situations where blood flow velocity is measured, but is suitable for wearable apparatuses that can be worn by the measurement subject in daily life environments.

For example, the main cause of body motion noise during exercise such as walking, jogging, and running is the periodic movement of the arm. Therefore, by measuring the movement of the arm with an acceleration sensor or the like and using it as a reference signal, it is possible to reduce the body motion noise mixed in the blood flow velocity information. However, in a case where the blood flow velocity is constantly measured in daily life, the body motion noise is often caused by aperiodic movements of fingers, wrists, or the like, and few are caused by periodic movements of the arm. Therefore, the range of the body motion noise that can be reduced by using an acceleration sensor or the like is narrow as described above, and it is difficult to constantly and accurately detect changes in blood flow velocity in the environment of daily life.

On the other hand, the biometric information processing apparatus of the present technology can effectively reduce the body motion noise generated in daily life regardless of the nature of the body motion noise such as whether or not it is periodic. Furthermore, the biometric information processing apparatus of the present technology can be reduced in size by using the LDF technology or the like, and can also perform non-invasive and continuous measurement. Therefore, the biometric information processing apparatus of the present technology is suitable for wearable apparatuses, and specifically suitable for wearable blood flow meter. A wearable blood flow meter using the present technology can robustly detect changes in blood flow velocity even during actions that occur in daily life.

Changes in blood flow velocity are known as indices of a person's health and psychological state. Therefore, the biometric information processing apparatus of the present technology can also be used in a wearable apparatus, an application, a system, and the like that senses a health state and/or a psychological state.

3. First Variation Example of the First Embodiment

Regarding the operation of a biometric information processing apparatus 1A according to the first variation example of the first embodiment, the point different from the first embodiment described above will be described with reference to FIG. 12.

Figure 12:
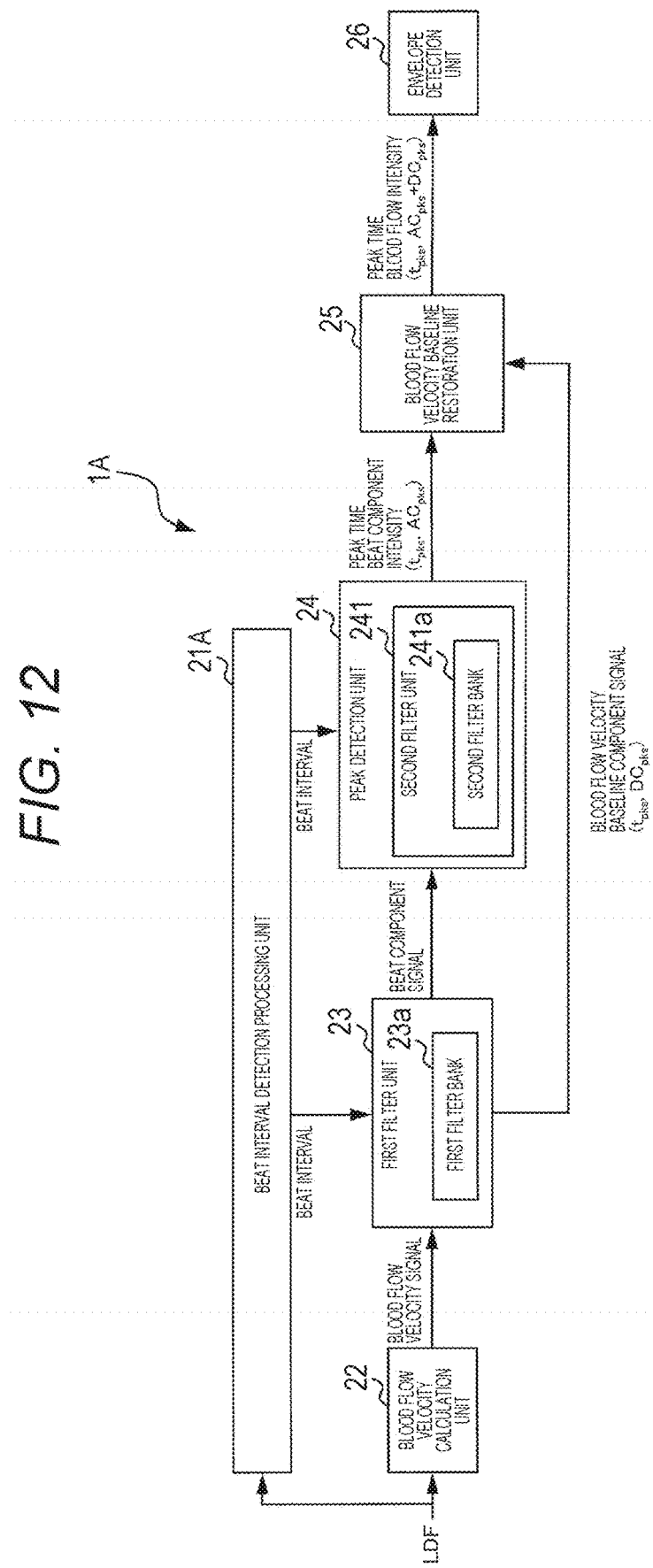
FIG. 12 is a block diagram showing an example of a functional configuration of a biometric information processing apparatus according to a first variation example of the first embodiment.

FIG. 12 is a block diagram showing an example of a functional configuration of the biometric information processing apparatus 1A according to the first variation example of the first embodiment. The biometric information processing apparatus 1A of the present variation example includes a beat interval detection processing unit 21A instead of the heart rate variability detection unit 21 of the first embodiment described above. The beat interval detection processing unit 21A is realized by the control unit 20 (FIG. 2).

The beat interval detection processing unit 21A executes a beat interval detection process of detecting the beat interval of the measurement subject, and outputs the beat interval. The beat interval detection processing unit 21A calculates and outputs the beat interval using, for example, a signal of the reflected light of laser light output from the LDF.

Since the biometric information processing apparatus 1A of the present variation example does not require other apparatuses such as PPG and ECG illustrated in the first embodiment described above, the configuration can be further simplified.

4. Second Variation Example of the First Embodiment

Regarding the operation of a biometric information processing apparatus 1B according to the second variation example of the first embodiment, the point different from the first embodiment described above will be described with reference to FIG. 13.

Figure 13:
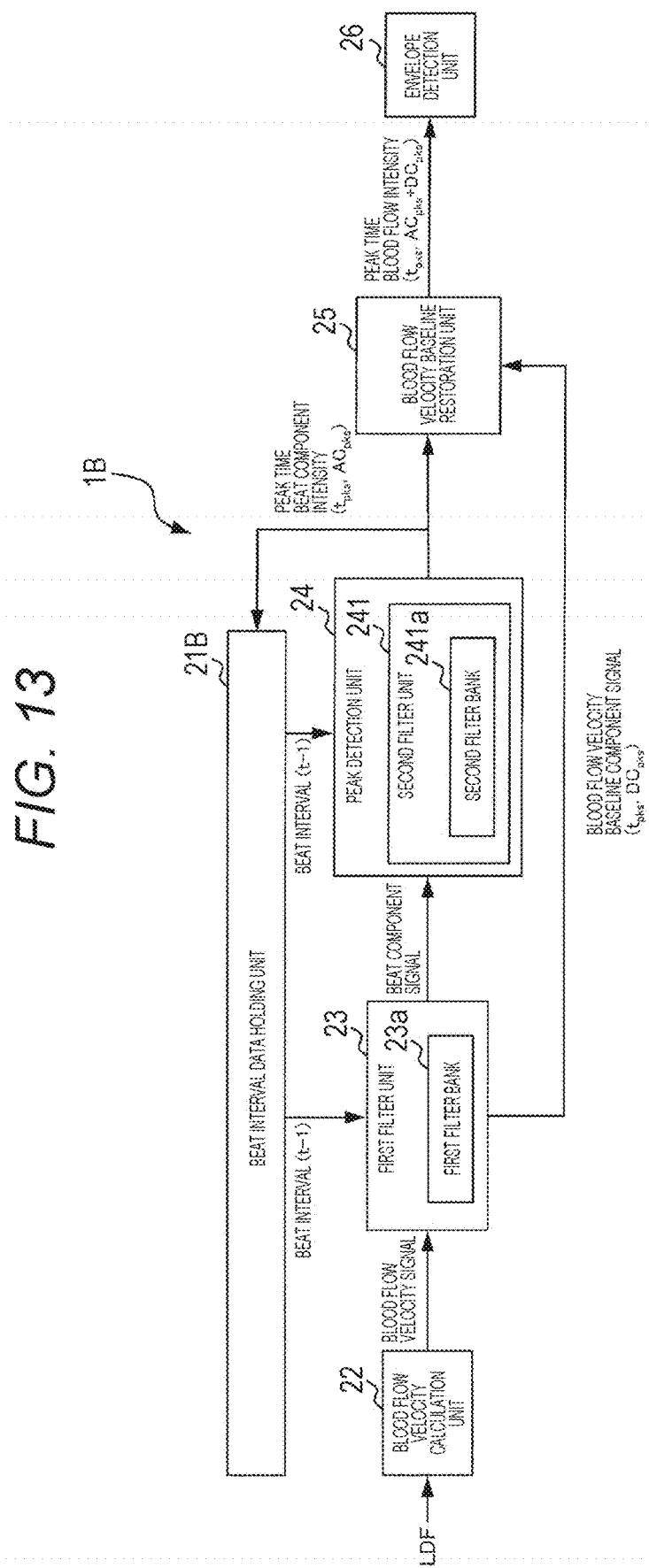
FIG. 13 is a block diagram showing an example of a functional configuration of a biometric information processing apparatus according to a second variation example of the first embodiment.

FIG. 13 is a block diagram showing an example of a functional configuration of the biometric information processing apparatus 1B according to the second variation example of the first embodiment. The biometric information processing apparatus 1B of the present variation example includes a beat interval data holding unit 21B instead of the heart rate variability detection unit 21 of the first embodiment described above. The beat interval data holding unit 21B is realized by the control unit 20 (FIG. 2).

The beat interval data holding unit 21B executes beat interval data holding processing that calculates and holds the beat interval on the basis of past detection results of the peak detection unit 24. The past detection result of the peak detection unit 24 is, for example, the peak time, the beat component intensity, and the like detected in the past by the peak detection unit 24. The first filter unit 23 and the peak detection unit 24 perform processing on the basis of past beat interval data held by the beat interval data holding unit 21B.

In the example shown in FIG. 13, the peak detection unit 24 uses past (time: t−1) beat interval data held by the beat interval data holding unit 21B in outputting beat component intensity ($t_{pks}$,$AC_{pks}$) at peak time ($t_{pks}$).

Since the biometric information processing apparatus 1B of the present variation example does not require other apparatuses such as PPG and ECG illustrated in the first embodiment described above, the configuration can be further simplified.

Note that the present technology may adopt the configuration described below.

[1] A biometric information processing apparatus including: a first filter unit that selects a first frequency band on the basis of a beat interval, causes a signal of the first frequency band from a blood flow velocity signal to pass through, and extracts a beat component signal.

[2] The biometric information processing apparatus according to [1], further including:
a peak detection unit that detects a peak position of the beat component signal and outputs peak time and beat component intensity at the peak time, in which the peak detection unit
detects the peak position of the beat component signal on the basis of the beat interval and holds the beat component intensity as history information except when body motion occurs, determines whether or not detection of the peak position is erroneous on the basis of the history information after detecting the peak position of the beat component signal on the basis of the beat interval and the history information when body motion occurs, and, in a case where the detection of the peak position is erroneous, corrects the peak position by using the beat interval and corrects the beat component intensity by using the history information.

[3] The biometric information processing apparatus according to [1] or [2], in which the first filter unit includes a first filter bank including a plurality of bandpass filters and uses a bandpass filter selected from the first filter bank on the basis of the beat interval to extract the beat component signal.

[4] The biometric information processing apparatus according to [2], in which the peak detection unit includes a second filter unit that selects a second frequency band on the basis of the beat interval except when body motion occurs, causes a signal of the second frequency band from the beat component signal to pass through, and detects the peak position of the beat component signal.

[5] The biometric information processing apparatus according to [4], in which the second filter unit includes a second filter bank including a plurality of bandpass filters and uses a bandpass filter selected from the second filter bank on the basis of the beat interval to detect the peak position of the beat component signal except when body motion occurs.

[6] The biometric information processing apparatus according to [2], in which when body motion occurs, in a case where the detection of the peak position is erroneous, the peak detection unit calculates likelihood of probability distribution of the peak position according to the beat interval, and sets a peak position where the likelihood is maximum as a corrected peak position.

[7] A biometric information processing method including: a first filter process of selecting a first frequency band on the basis of a beat interval, causing a signal of the first frequency band from a blood flow velocity signal to pass through, and extracting a beat component signal.

REFERENCE SIGNS LIST 1, 1A, 1B Biometric information processing apparatus
10 Blood flow sensor unit
20 Control unit
21 Heart rate variability detection unit
21A Beat interval detection processing unit
21B Beat interval data holding unit
22 Blood flow velocity calculation unit
23 First filter unit
23a First filter bank
24 Peak detection unit
241 Second filter unit
241a Second filter bank
25 Blood flow velocity baseline restoration unit
26 Envelope detection unit

The invention claimed is:

1. A biometric information processing apparatus, comprising:
a blood flow velocity calculation unit configured to:
acquire a beat signal;
execute a blood flow velocity calculation process based on the beat signal; and
output a blood flow velocity signal based on the execution of the blood flow velocity calculation process; and
a first filter unit configured to:
acquire beat interval information;
select a first frequency band based on the beat interval information;
execute a first filter process on the blood flow velocity signal based on the first frequency band; and
extract, based on the execution of the first filter process, a first signal, of the first frequency band, from the blood flow velocity signal, wherein the first signal is extracted as a beat component signal.

2. The biometric information processing apparatus according to claim 1, further comprising a peak detection unit configured to determine one of an occurrence of body motion of a subject or a non-occurrence of the body motion, wherein
in a case of the determination of the non-occurrence of the body motion, the peak detection unit is further configured to:
detect a first peak position of the beat component signal based on the beat interval information;
output, based on the detected first peak position, each of:
a first peak time of the beat component signal, and
a first beat component intensity, of the beat component signal, at the first peak time; and
store the first beat component intensity as first history information, and
in a case of the determination of the occurrence of the body motion, the peak detection unit is further configured to:
detect a second peak position of the beat component signal based on the beat interval information and second history information;
determine, based on the second history information, that the detection of the second peak position is erroneous;
correct the second peak position based on the beat interval information and the determination that the detection of the second peak position is erroneous; and
correct a second beat component intensity of the beat component signal based on the second history information.

3. The biometric information processing apparatus according to claim 1, wherein
the first filter unit includes a first filter bank including a plurality of bandpass filters, and
the first filter unit is further configured to:
select a bandpass filter from the first filter bank based on the beat interval information; and
extract the beat component signal based on the selected bandpass filter.

4. The biometric information processing apparatus according to claim 2, wherein
the peak detection unit includes a second filter unit, and
the second filter unit is configured to:
select a second frequency band based on the beat interval information and the determination of the non-occurrence of the body motion;
execute a second filter process to extract a second signal, of the second frequency band, from the beat component signal; and detect, based on the execution of the second filter process, the first peak position of the beat component signal.

5. The biometric information processing apparatus according to claim 4, wherein
the second filter unit includes a second filter bank including a plurality of bandpass filters, and
the second filter unit is further configured to:
select a bandpass filter from the second filter bank based on the beat interval information; and
detect the first peak position of the beat component signal based on the selected bandpass filter and the determination of the non-occurrence of the body motion.

6. The biometric information processing apparatus according to claim 2, wherein in a case of the determination of the occurrence of the body motion and the determination that the detection of the second peak position is erroneous, the peak detection unit is further configured to:
calculate likelihood of probability distribution of the second peak position based on the beat interval information; and
set a third peak position where the likelihood is maximum as a corrected peak position.

7. The biometric information processing apparatus according to claim 1, wherein the blood flow velocity signal indicates a blood flow velocity of a subject.

8. A biometric information processing method, comprising:
acquiring a beat signal;
executing a blood flow velocity calculation process based on the beat signal;
outputting a blood flow velocity signal based on the execution of the blood flow velocity calculation process;
acquiring beat interval information;
selecting a first frequency band based on the beat interval information;
executing a filter process on the blood flow velocity signal based on the first frequency band; and
extracting, based on the execution of the filter process, a signal, of the first frequency band, from the blood flow velocity signal, wherein the signal is extracted as a beat component signal.

* * * * *